United States Patent [19]

Al-Shamkhani et al.

[11] Patent Number: 5,622,718
[45] Date of Patent: Apr. 22, 1997

[54] ALGINATE-BIOACTIVE AGENT CONJUGATES

[75] Inventors: Aymen Al-Shamkhani, Oxford; Ruth Duncan, London, both of United Kingdom

[73] Assignee: Keele University, Staffordshire, England

[21] Appl. No.: 406,876

[22] PCT Filed: Sep. 23, 1993

[86] PCT No.: PCT/GB93/01999

§ 371 Date: Apr. 28, 1995

§ 102(e) Date: Apr. 28, 1995

[87] PCT Pub. No.: WO94/07536

PCT Pub. Date: Apr. 14, 1994

[30] Foreign Application Priority Data

Sep. 25, 1992 [GB] United Kingdom ............ 9220294

[51] Int. Cl.$^6$ ............................................. A61K 47/48
[52] U.S. Cl. ............... 424/488; 525/54.2; 525/54.3; 536/3
[58] Field of Search ............ 424/488; 525/54.2, 525/54.3; 536/3

[56] References Cited

U.S. PATENT DOCUMENTS

| | | | |
|---|---|---|---|
| 4,003,792 | 1/1977 | Mill et al. | 195/63 |
| 4,631,190 | 12/1986 | Shen et al. | 424/85 |
| 5,013,669 | 5/1991 | Peters et al. | 436/518 |
| 5,037,883 | 8/1991 | Kopecek et al. | 525/54.1 |

FOREIGN PATENT DOCUMENTS

| | | |
|---|---|---|
| 1014046 | 12/1965 | United Kingdom . |
| 1174854 | 12/1969 | United Kingdom . |
| 1515562 | 6/1978 | United Kingdom . |

OTHER PUBLICATIONS

Taylor et al, Immunology, vol. 44, No. 1, pp. 41–50 (1981).
Bruno et al, Annals of Allergy, vol. 56, No. 5, pp. 384–391 (1986).
Boye et al, Allergy, vol. 45, No. 4, pp. 241–248 (May 1990).
Coin et al, Fems, vo. 76, No. 4, pp. 185–192 (1991).
Ortolani et al, J. Allergy and Clinical Immunology, vol. 81, No. 1 (1988).
Pastorelo et al, Folia Allergol Immunol. Clinica, vol. 37, No. 3, pp. 135–142 (1990).
Hoiby et al, Cystic Fibrosis, Basic and Clinical Research, Jun. 1991.
Pastorello et al, J. Allergy and Clinical Immunology, vol. 77, No. 1, Part 2, (Jan. 1986).
Shen et al, Biochem. Biophys. Res. Commun., vol. 102, No. 3, pp. 1048–1054 (1981).
Mann et al, Bioconjugate Chem., vol. 3, No. 2, pp. 154–159 (1992).
Lavie et al, Cancer Immunol. Immunother, vol. 33, No. 4, pp. 223–230 (1991).
Diener et al, Science (USA), vol. 231, No. 4734, pp. 148–150 (1986).
Gaureault et al, Anticancer Research, vol. 9, No. 4, pp. 1201–1206 (1989).
Dillman et al, Cancer Research, vol. 48, No. 21, pp. 6097–6102 (1988).
Bianchi et al, Contributions to Nephrology, vol. 101, pp. 99–103 (1991).
Abstract from Derwent World Patents Index, Acc. No. 87–311548/44 (J62221637-A (Sep. 29, 1987)).
Abstract from Derwent World Patents Index, Acc. No. 89–035245/05 (J63307823-A (Dec. 16, 1988)).
Abstract from Derwent World Patents Index, Acc. No. 78–75318A/42 (J53104715-A (Dec. 9, 1978)).

Primary Examiner—Nathan M. Nutter
Attorney, Agent, or Firm—Cushman Darby & Cushman IP Group Pillsbury Madison & Sutro LLP

[57] ABSTRACT

The invention is an alginate-bioactive agent conjugate connected via an acid labile biodegradable spacer linkage. The conjugate is effective for delivering bioactive agents to targets existing in low-pH environments, either at the target surface or in the target interior.

29 Claims, 3 Drawing Sheets

ALGINATE-BIOACTIVE AGENT CONJUGATES

BACKGROUND OF THE INVENTION

One of the significant drawbacks of antitumor or antineoplastic agents is their failure to discriminate between normal dividing cells and tumor cells. When acting on normal dividing cells, these agents cause undesireable side effects, including nausea, apolecia, and bone marrow toxicity. Their cardiotoxicty is a primary contributor to dosage limitation.

Kopecek et al., U.S. Pat. No. 5,037,883, describe a drug conjugate which includes inert synthetic N-(2 hydroxypropyl) methacrylamide polymeric carriers combined through peptide spacers with a bioactive molecule, with a targeting moiety, and with an optional cross-linkage. The peptide spacers contain between 2 and 6 naturally occurring amino acids.

Yang et al., *Proc. Natl. Acad. Sci.* USA vol. 85, pp. 1189–1193 (1988) describe doxorubicin conjugated with a monoclonal antibody directed to a human melanoma-associated proteoglycan. The conjugate suppresses the growth of established tumor xenografts in nude mice.

Dillman et al., *Cancer Research* vol. 48, pp. 6097–6102 (1988) describe the superiority of an acid-labile daunorubicin-monoclonal antibody immunoconjugate compared to free acid.

Shen et al., *Biochemical and Biophysical Research Communications* vol. 102, no. 3, pp. 1048–1054 (1981) describe cis-aconityl spacer between daunomycin and macromolecular carriers.

SUMMARY OF THE INVENTION

The invention is an alginate-bioactive agent conjugate which comprises:

(a) an alginate or alginate derivative; and (b) a bioactive agent, wherein the alginate and the bioactive agent are connected via a biodegradable spacer linkage. Preferably, the linkage is an acid labile linkage.

The present invention also comprises pharmaceutical compositions which comprise at least one conjugate of the invention and an inert, physiologically acceptable carrier. The compositions can be administered orally or by injection, for example by intraperitoneal, intravenous or intramuscular injection.

DETAILED DESCRIPTION OF THE INVENTION

The invention permits combination of controlled release of a bioactive material and the beneficial biological properties of alginates. Non-toxic alginates display inherent properties which provoke beneficial pharmacological activity and when covalently bound to a bioactive material (including drugs and prodrugs), alginates can be used to control the rate of release of the material.

Alginate, as used herein, refers to sodium alginate, alginic acid sodium salt of algin (see page 41, The Merck Index, 11$^{th}$ Edition (1989), Merck & Co., Inc.) Alginates are gelling polysaccharides extracted from giant brown seaweed (*Macrocysris pyrifera*) or horsetail kelp (*Laminaria digitata*) or from sugar kelp (*Laminaria saccharina*). In seaweed, polysaccharides are present as a mixed sodium and/or potassium, calcium and magnesium salt. Alginates are commercially available from Kelco, a Division of Merck & Co., Inc. (San Diego, Calif.).

Various alginates useful in this invention are described in detail by I. W. Cottrell and P. Kovacs in "Alginates", Chapter 2 of Davidson, ed., Handbook of Water-Soluble Gums and Resins (1980). Most preferred herein are naturally derived algal sodium alginates (also called "algin" or "alginic acid sodium salt"), such as those sold commercially under the trademarks KELTEX®, KELGIN® and KELTONE™ by Kelco Division of Merck & Co., Inc.

Alginates also include "bioalgin", microbially produced polysaccharides produced by both Pseudomonas and Azotobacter strains as described, for example, in Jannan et al., U.S. Pat. No. 4,235,966. These alginates are polysaccharides consisting of a partially acetylated variable block copolymer of D-mannuronic and L-guluronic acid residues. Jarman et al. state that the polysaccharide produced is similar to that produced from seaweed except that the molecule is partially acetylated.

Alginates contain both mannuronic acid and guluronic acid. The presence of three kinds of polymer segments in alginic acid from various brown algae has been shown. One segment consists essentially of D-mannuronic acids units; a second segment consists essentially of L-guluronic acid traits; and the third segment consists of alternating D-mannuronic acid and L-guluronic acid residues.

The proportions of the three polymer segments in alginic acid samples from different sources have been determined using partial acid hydrolysis to separate the alginic acid into homopolymeric and alternating segments.

One of the most important and useful properties of alginates is the ability to form gels by reaction with calcium salts. These gels, which resemble a solid in retaining their shape and resisting stress, consist of almost 100% water (normally, 99.0 to 99.5% water and 0.5 to 1.0% alginate).

A gel, in classical colloid terminology, is defined as a system which owes its characteristic properties to a cross-linked network of polymer chains which form at the gel point.

Alginates have the ability to stimulate the production of cytokines such as tumor necrosis factor-alpha, interleukin-6, and interleukin-1. In one embodiment of the invention, alginates are conjugated to antitumor agents. Conjugation of the antitumor agent to alginate effectively improves the therapeutic index of the drug by controlling release while the alginate carrier stimulates an antitumor cellular immune response.

In another embodiment of the invention, alginates are conjugated to antibiotics. These conjugated antibiotics are especially useful for treating superficial wounds. The conjugate effectively controls the release of the antibiotic at the site of injury, and the alginates promote wound healing.

The invention is an alginate-bioactive agent conjugate which comprises:

(a) an alginate or alginate derivative; and (b) a bioactive agent, wherein the alginate and the bioactive agent are covalently bound via a biodegradable linkage such as an acid labile linkage.

The conjugates of the invention may be administered to organisms, including mammals, preferably in combination with pharmaceutically acceptable carriers or diluents, optionally with known adjuvants such as alum, in a pharmaceutical composition which is non-toxic and in a therapeutically effective amount, according to standard pharmaceutical practice. The compounds can be administered orally, parenterally (e.g. by intravenous, subcutaneous, intramuscular, or intramedullary injection), topically, or percutaneously (e.g. by diadermic, transcutaneous, or transdermic procedures).

For oral use, the conjugates may be administered, for example, in the form of tablets or capsules, or as an aqueous solution or suspension. In the case of tablets for oral use, carriers which are commonly used include lactose and corn starch. Lubricating agents, such as magnesium stearate, are also commonly used. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. Alginate-bioactive agent conjugates can be mixed, for example, with alginate, and subsequently gelled by the addition of $CaCl_2$ to form alginate beads. Alginates behave differently at varying pH levels (between 2 and 7) which allows for further control of drug release.

For intramuscular, intraperitonial, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

Preferably, the alginate comprises a first segment consisting essentially of D-mannuronic acid residues, a second segment consisting essentially of L-guluronic acid residues, and a third segment consisting essentially of alternating D-mannuronic acid and L-guluronic acid residues.

The molecular weight of the alginate must be large enough to prevent rapid passage through the kidney of the patient and yet small enough to assure passage within a reasonable time. The alginate molecular weight is preferably between about 2,000 and 1,000,000. More preferred molecular weights depend on the method of administration of the bioactive material. For bioactive materials which are administered parenterally, alginates having molecular weights of between about 5,000 and 100,000 are preferred. For bioactive materials which are administered orally, such as in a capsule or tablet, higher molecular weight alginates, between 200,000 and 1,000,000, are preferred.

The alginate preferably has attached amino groups to which the conjugate linkage is attached.

The preferred bioactive agent is selected from the group of antitumor agents and antibiotics. The preferred antitumor agent is a cytotoxic drug such as an anthracycline or derivative thereof. The anthracycline is preferably daunombicin (also referred to as daunomycin or Dnm), doxorubicin, epirubicin or derivatives thereof, more preferably, daunombicin. The preferred antibiotic is amoxycillin or ampicillin.

Other suitable bioactive materials are those having functional $NH_2$ groups for binding the alginate, such as bioactive proteins or peptides, or other therapeutic compounds which are first modified to include the appropriate functional group, e.g. 5-aminosalycilic acid, prior to conjugation with the alginate.

The acid labile linkage is physiologically stable at vascular pH of about 7.4 and hydrolytically cleaves under acidic condition. Release of the drug to which the alginate is conjugated occurs in any acidic environment, such as a mammal's gastrointestinal tract, at the site of inflammation, inside a minor mass, or intracellularly.

Preferably, the acid labile linkage between the drug and alginate is a cis-aconityl group having the formula wherein the group is attached to drug via peptide bond and attached to alginate via peptide bond.

Preferably, when the bioactive material is a cytotoxic drug, the conjugates of the present invention preserve cytotoxic pharmacological activity and allow pH dependent release. The conjugate releases the cytotoxic agent in the acidic milieu of the endosome/lysosome and the acidic environment or surroundings of the tumor. The toxicity of the cytotoxic agent is reduced as the complex is not hydrolyzed in the plasma at neutral pH.

The invention is also a method for releasing a cytotoxic drug in an acidic environment comprising (a) introducing an alginate-cytotoxic drug conjugate comprising (i) an alginate or alginate derivative, and (ii) a cytotoxic drug, wherein the alginate and the cytotoxic drug are connected via an acid labile linkage, to a pH environment of about 7.4;

(b) modifying the pH environment of the conjugate by decreasing the pH; and (c) hydrolyzing the alginate-cytotoxic drug conjugate linkage.

The invention is also a method for releasing a cytotoxic drug in an acidic environment comprising (a) introducing an alginate-cytotoxic drug conjugate comprising (i) an alginate or alginate derivative, and (ii) a cytotoxic drug, wherein the alginate and the cytotoxic drug are connected via an acid labile linkage, into an acidic body compartment, such as a stomach or tumor cell; and (b) hydrolyzing the alginate-cytotoxic drug conjugate linkage.

The invention is also a method for delivering a cytotoxic drug to a tumor which comprises (a) introducing to the tumor cell surface an alginate-cytotoxic drug conjugate comprising (i) an alginate or alginate derivative, and (ii) a cytotoxic drug, wherein the alginate and the cytotoxic drug are connected via an acid labile linkage; and, (b) hydrolyzing the alginate-cytotoxic drug conjugate linkage in the low pH surroundings of the minor surface to release the cytotoxic drug to the tumor surroundings and absorbing the cytotoxic drug through the cellular membrane.

The invention is also a method for treating a neoplastic condition in a patient having a tumor which comprises (a) introducing an alginate-cytotoxic drug conjugate comprising (i) an alginate or alginate derivative, and (ii) a cytotoxic drug, wherein the alginate and the cytotoxic drug are connected via an acid labile linkage, to a patient having a neoplastic condition; and (b) hydrolyzing the alginate-cytotoxic drug conjugate linkage in the low pH surroundings of the tumor surface to release the cytotoxic drug to the tumor surroundings and absorbing the cytotoxic drug through the cellular membrane.

The invention is also a method for delivering a cytotoxic drug to a tumor which comprises (a) introducing an alginate-cytotoxic drug conjugate comprising (i) an alginate or alginate derivative, and (ii) a cytotoxic drug, wherein the alginate and the cytotoxic drug are connected via an acid labile linkage, to the tumor cell surface;

(b) internalizing the conjugate by endocytosis into the tumor; and, (c) hydrolyzing the alginate-cytotoxic drug conjugate linkage in the low pH environment of the tumor interior to release the cytotoxic drug inside the tumor.

The invention is also a method for treating a neoplastic condition in a patient having a tumor which comprises (a) introducing an alginate-cytotoxic drug conjugate comprising (i) an alginate or alginate derivative, and (ii) a cytotoxic drug, wherein the alginate and the cytotoxic drug are connected via an acid labile linkage, to the tumor cell surface;

(b) internalizing the conjugate by endocytosis into the tumor; and, (c) hydrolyzing the alginate-cytotoxic drug conjugate linkage in the low pH environment of the tumor interior to release the cytotoxin inside the tumor.

The general strategy for preparing the conjugate

Alginate -S'-B' wherein S' is a pH sensitive biodegradable linker and B' is a bioactive agent, is as follows:

a) S'+B'-NH$_2$→HOOC-S'-B'

EDC b) Alginate→"Alginate"

c) "Alginate"+ethylenediamine→Alginate-NH$_2$

EDC d) HOOC-S'-B'→"S'-B'"

e) Alginate-NH$_2$+"S'-B'"→Alginate-S'-B'

"Alginate" is activated alginate, and "S'-B'" is activated S'-B'. EDC is 1-ethyl-3-(3-dimethylaminopropyl)-carbodiimide.

Generally, the procedure for preparing alginate-bioactive agent conjugates, preferably alginate-cytotoxic drug conjugates, involves the steps of:

a) combining the linker with the cytotoxic drug to form a linker-modified cytotoxic drug;

b) activating the alginate with 1-ethyl-3-(3-dimethylaminopropyl)-carbodiimide;

c) combining activated alginate with ethylenediamine to form alginates having free primary amine groups (alginate-NH$_2$);

d) activating the linker-modified cytotoxic drug with 1-ethyl-3-(3-dimethylaminopropyl)-carbodiimide; and e) combining activated linker-modified cytotoxic drug with alginate-NH$_2$ to form the alginate-cytotoxic drug conjugate.

Alginates

Alginates of various molecular weights are commercially available from Kelco. Molecular weights can also be modified according to the following procedure.

Preparation of low molecular weight Alginates

A method to obtain alginates with a molecular weight of ~100 kDa is described below. Low molecular weight alginates (identified below as F1, F2, and F3, were produced by controlled degradation of alginate(56) (alginate having a molecular weight of about 427 kDa) as follows: samples of alginate(56) dissolved in acetic acid (1% v/v) were subjected to the following conditions:

(a) Heating to 121° C. for 15 minutes, or (b) Heating to 105° C. for 5 minutes, or (c) Heating to 100° C. for 5 minutes.

The resulting solutions were neutralized and then dialyzed extensively against distilled water, followed by freeze drying and then analysis by SE-HPLC. The appropriate alginates (~131 kDa) were obtained by heating to 100° C. for 5 minutes.

The following table describes various alginates used to prepare conjugates of the present invention.

| Alginate samples | | | | |
|---|---|---|---|---|
| Reference | M/G | Seaweed species | Mw | Mw/Mn |
| 56 | high | *Macrocystis pyrifera* | 427000 | 3.1 |
| 55 | low | mixture of high "G" seaweeds | 763000 | 2.9 |
| 58 | high | *Macrocystis pyrifera* | 689000 | 2.7 |
| Asco | high | *Ascophyllum nodosum* | 690000 | 3.5 |
| Flavi | low | *Lessonia flavicans* | 797000 | 2.9 |
| F1 | — | from alginate(56) | 131000 | 2.8 |
| F2 | — | from alginate(56) | 56000 | 2.9 |
| F3 | — | from alginate(56) | 10000 | 1.9 |

M/G is mannuronic acid:guluronic acid ratio. Mw is average molecular weight as determined by size exclusion—HPLC using pullulan standards. Mw/Mn is polydispersity. High "G" seaweeds include *Lessonia flavicans* and *Laminaria hyperborea*. Alginate(58) is propylene glycol alginate.

Biocompatibilty assessment of various alginates by the MTT assay

The assay, used for evaluating polymers and drugs, is based on the ability of viable cells to reduce a soluble tetrazolium dye, MTT, to colored water insoluble formazan crystals. The assay was carried out in 96-well microliter plates (flat bottomed).

At confluence, B16F10 cells were detached as follows: following removal of the medium, cells were washed twice with sterile PBS to remove excess medium. Trypsin-EDTA solution (2 ml) was added and the flasks were agitated gently for 30 seconds. The trypsin-EDTA solution was then removed using a Pasteur pipette connected to a vacuum line and the cells incubated at 37° C. for 1 minute to allow detachment. Cells were suspended in medium (5ml/flask) and diluted accordingly to give a concentration of $10^4$ cells/ml.

Medium containing cells (200 μl) were dispensed by a multichannel pipette into each well with the exception of the first row wells which were filled with medium only (200 μl) and were designated "blank" wells (used for zeroing with the microliter plate reader). A seeding density of $10^4$ cells/ml was previously found optimal to B16F10 cells since polymers/drugs could be added 24 hours after cell plating, just as cells were beginning to enter their exponential phase and the MTT assay performed 72 hours later giving a mean value for the absorbance of formazan of approximately 1.5 for the untreated controls. Following an incubation of 24 hours at 37° C. (5% $CO_2$), the medium was removed by aspiration and in some wells replaced by medium containing polymers/drugs at various concentration (200 μl, 6 replicates). The remaining wells were replaced with medium only (200 μl) and designated "untreated controls." Due to the poor solubility of alginates in the growth medium-MEM (due to the presence of high concentration of divalent metals), all alginate stock solutions (10 mg/ml) were prepared in Ham's F10 medium, supplemented with foetal calf serum (10% v/v) and L-glutamine (1% v/v). The stock solutions were then sterilized by filtration (Flowpore D, 0.2 μm filter) and diluted with MEM prior to addition to cells. Any detrimental effects on the cells due to Ham's F10 medium were accounted for by control wells where Ham's F10 medium was diluted in the same ratio with MEM and then added to cells.

Following a 67 hour incubation (37° C., 5% $CO_2$), a sterile solution of MTT (20 μl, 5 mg/ml in PBS) was added to each well, and the plates were placed in the incubator for a further 5 hour period (72 hour in total). At the same time period, the medium was removed with the aid of a hypodermic needle connected to a vacuum line. The formazan crystals were dissolved by the addition of spectrophotometric grade DMSO (200 μl) to each well and the absorbance determined at 550 nm using a microtitre plate reader.

The results of each treatment were expressed as a percentage of the appropriate controls (untreated cells).

The following alginates were tested against the mouse melanoma cell line B16F10:

| Alginate | concentration range (mg/ml) |
| --- | --- |
| 56 | 0.1–5.0 |
| 55 | 0.1–5.0 |
| 58 | 0.1–5.0 |
| Asco | 0.1–2.5* |
| Flavi | 0.1–1.0* |
| Alginate 427 kDa | 0.05–1.0 |
| Alginate 90 kDa | 0.05–1.0 |
| Alginate 35 kDa | 0.05–1.0 |
| F3 | 0.05–1.0 |

*higher concentrations could not be used as they were too viscous to be filtered through 0.2 m filters.

All the alginates tested were not toxic at the concentrations used in these experiments, with the exception of propyleneglycol alginate (PGA) which was toxic at 5 mg/ml. As expected, poly-L-lysine was toxic at even very low concentrations. The toxicity of PGA may be due to covalent coupling of cell surface membrane proteins due to the reaction of the primary amine groups of proteins with the reactive ester groups of the polymer. This could lead to membrane perturbation and eventually cell death. Toxicity may have also resulted from propyleneglycol which is likely to be released from the alginates upon incubation in tissue culture.

EXAMPLE 1

Preparation of alginate-$NH_2$

Alginate(56) (500 mg) was dissolved in water (50 ml) and pH adjusted to 4.75 with HCl (0.1M). Solid 1-ethyl-3-(3-dimethylaminopropyl)carbodiimide (EDC) (60 mg), was added and pH kept constant by addition of HCl (0.1M). After 1 h, the solution was added dropwise to a solution containing a 40-fold excess of ethylene diamine. The pH was adjusted to 4.75 with NaOH (0.1M) and the solution left stirring at room temperature. One hour later, the pH was raised to 6 and the mixture left siring for another hour. The pH was then increased to 12 with NaOH (5M) and NaCl (4.5 g) was added. This was necessary, in order to dissociate electrostatically bound diamine. The final solution was then extensively dialysed, firstly against carbonate buffer (pH 11.3) and then against distilled water.

A control was also carried out where alginate was mixed with ethylene diamine without prior activation with EDC. Using an identical protocol, alginate-tyrosinamide containing amine groups was produced.

The amine content of the polymers was estimated by the o-phthaladehyde method.

Preparation of biactive agents for conjugation to alginate-$NH_2$ N-cis-aconityl-Daunomycin (N-cis-aconityl-Dnm)

Dnm (6 mg) was dissolved in 1 ml $Na_2HPO_4$ buffer (pH 9.0) and kept on ice. cis-Aconitic anhydride (10 mg) was then added slowly while stirring, and the pH was kept at 9 by the addition of NaOH (0.5M). The solution was mixed at 0° C. for 10 minutes and then at room temperature for 15 minutes. The reaction mixture was then made up to 3 ml with water and left on ice.

N-cis-aconityl-Dnm was precipitated with HCl (1.0M) and kept on ice for 0.5 hours. After centrifugation, the precipitate was dissolved in water with small additions of NaOH (0.1M). The purification procedure was repeated and the final precipitate was dissolved in water (0.5 ml) with small additions of NaOH (0.1M). The concentration of the product was determined by measuring the absorbance at 475 nm. The product was checked by TLC (solvent: dichloromethane/methanol/acetic acid/water—30:4:1:0.5).

Synthesis of Alginate-Daunomycin Conjugates

The anthracycline antibiotics are the most widely used antitumor agents. Daunomycin is mainly used in the treatment of leukemias, but as in the case of all antineoplastic agents, daunomycin does not discriminate well between normal dividing cells and tumor cells and is associated with side-effects such as nausea, apolecia and bone marrow toxicity. In addition daunomycin shows cardiotoxicity which is often dose limiting.

Alginate-Dnm conjugates provide advantages over and above the existing conjugates. First, daunomycin is coupled to alginate via an acid-sensitive linker, cis-aconitic anhydride, which is stable at the vascular pH of 7.4. Once the macromolecular conjugate is endocytosed by the target cell, the drug is cleaved in the more acidic environment of the endosomes and lysosomes via a mechanism of hydrolyric cleavage. Second, the alginate carrier is biodegradable in vivo, and the carrier is therefore more easily removed from the organism.

Two types of alginates were used for this synthesis: high 'M' alginate(56) and alginate-tyrosmamide. The latter was used in order to radiolabel the conjugate with $^{125}I$ to enable us to study its pharmacokinetics.

To a solution of N-cis-aconityl-Dnm (pH 7.0) an equivalent amount of solid EDC was added. The solution was stirred for 20 minutes at room temperature and then alginate-$NH_2$ solution (1% w/v) was added dropwise with continuous stirring. The mixture was left reacting for 5 hours (Alginate-tyrosinamide-$NH_2$) or 24 hours (alginate(56)-$NH_2$).

Free daunomycin was separated from polymer bound on Sephadex G50 column (2.6×60 cm). The amount of bound daunomycin was determined by measuring the absorbance at 475 nm, and free daunomycin was found to be absent using TLC. The product structure is shown below:

Structure of Alginate-Daunomycin conjugate

Alginates containing free primary amine groups were successfully synthesized. The amount of ionically bound diamine was almost negligable.

| Polymer | Amine content (mole %) |
| --- | --- |
| Alginate(56) | 3.7 |
| Alginate(56) - control | 0.09 |
| Alginate-tyrosinamide | 4.5 |

When a sample of alginate-tyrosinamide-$NH_2$ was analyzed by SE-HPLC, it eluted at approximately the same retention time as the non-modified alginate, indicating that there was no cross-linking or degradation.

Synthesis of N-cis-aconityl-Dnm was confirmed by T.L.C. ($Rf_{Dnm}$=0.09, $Rf_{cisaconityl-Dnm}$=0.3). The amount of daunomycin bound to the alginate is shown below.

| Polymer | Dnm (%. w/w) |
| --- | --- |
| Alginate-tyrosinamide-Dnm | 2 |
| Alginate(56)-Dnm | 1 |

Free daunomycin was not detected by T.L.C. in either preparation ($Rf_{Alginate-Dnm}$=0). The daunomycin content of both polymers is low and only a small fraction of the free amine groups on the alginates reacted with the N-cis-aconityl-Dnm. This is likely to be at least in part due to steric hindrance. A higher drug content may be achieved by preparing an alginate with a higher amount of amine groups (>10 mol %), which can then be coupled to N-cis-aconityl-Dnm. If needed, alginates of lower molecular weight can be used.

EXAMPLE 2

Cytotoxicity of Alginate-Dnm conjugates

The effect of alginate, alginate-Dnm conjugates, daunomycin and poly-L-lysine on the viability of the mouse melanoma cell line B16F10 in vitro was assessed by the MTT assay. Unmodified alginates were not toxic even at concentrations as high as 5 mg/ml. Alginate-Dnm conjugates showed cytotoxic activity indicating that the drug activity was preserved throughout the conjugation reaction. The conjugates were approximately 500 fold less toxic than the free drug. This is expected since cellular entry of the conjugates is restricted to endocytosis, a slower process than the mechanism of entry of the free drug (diffusion). Futhermore, the toxicity observed in vitro was mainly due to the free drug in the preparation. This was estimated by RP-HPLC and was found to be 0.61% by weight of the total daunomycin bound to the alginates.

EXAMPLE 3

Controlled release of daunomycin from alginate-Dnm conjugates

Figure 1:
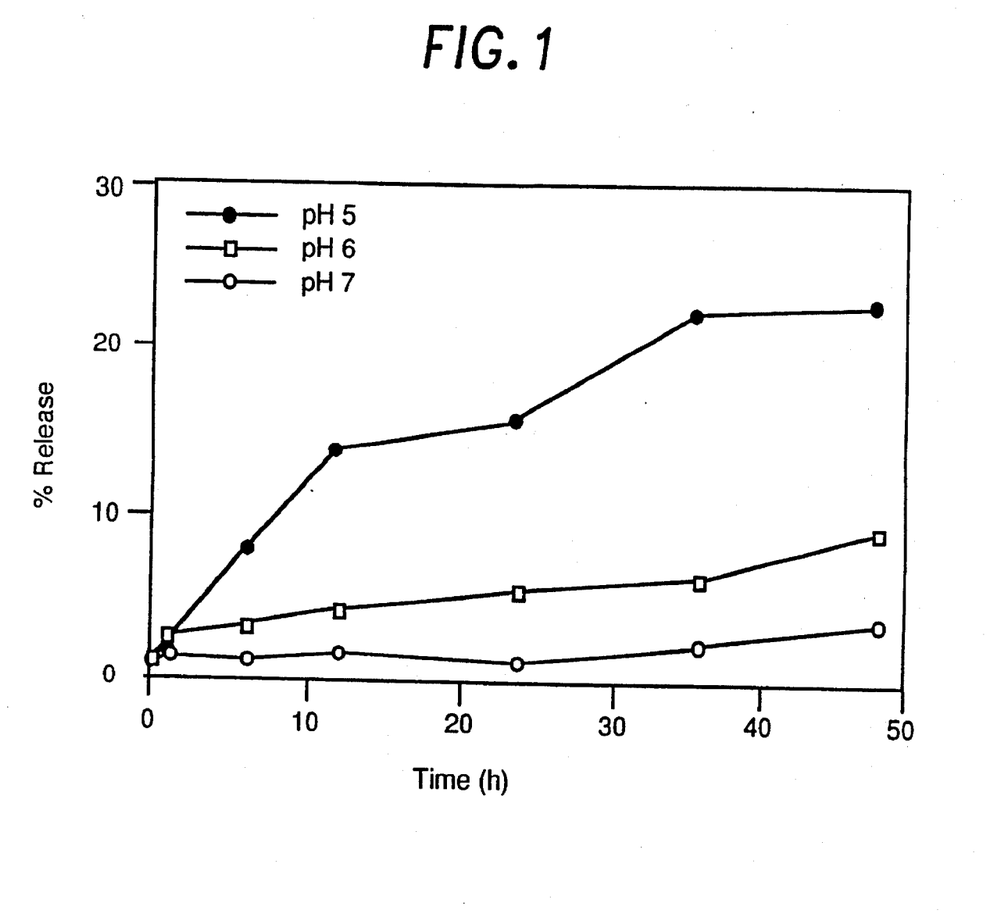
FIG. 1 shows percent daunomycin in vitro release over time.
Figure 2:
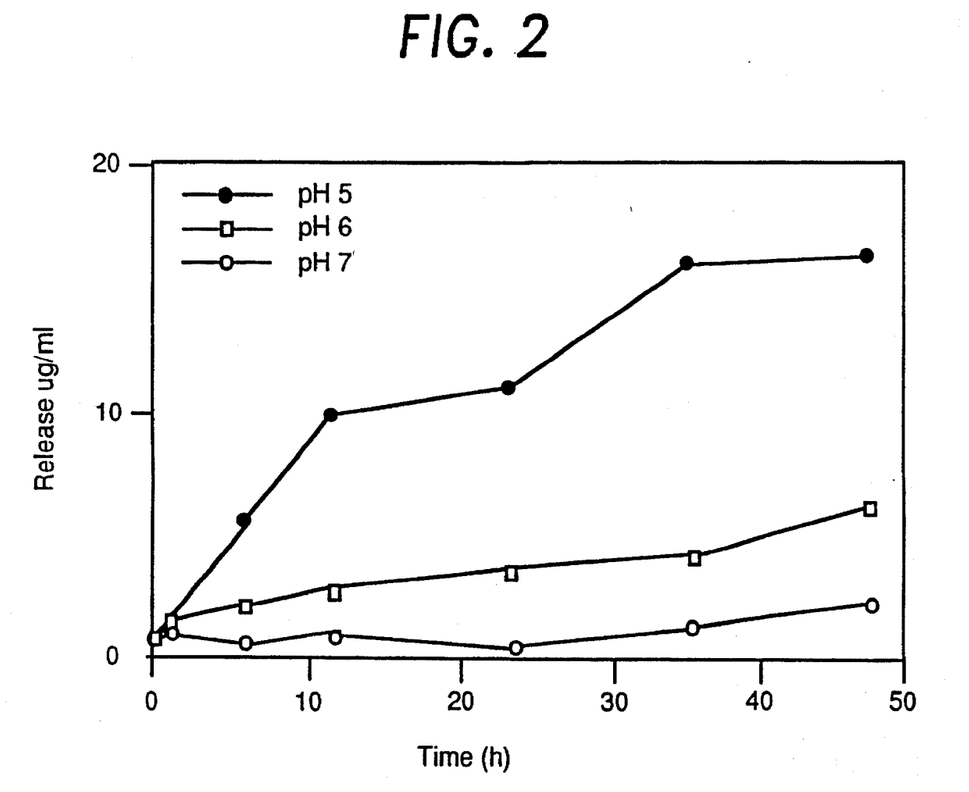
FIG. 2 shows μg/ml daunomycin in vitro release over time.

Samples of alginate(56)-Dnm conjugates were incubated at 37° C. in citrate/phosphate buffers at pH 5, 6 and 7 and the release of Dnm was followed by RP-HPLC analysis. The results showed that there was little Dnm released over 48 hours at pH 7. The rate of release increased as the pH decreased. At 48 hours approximately 8% (5.95 mg) and 23% (15.79 mg) of the total daunomycin was released at pH 6 and 5 respectively. FIG. 1 shows percent release profile, over 48 hours, of daunomycin from the alginate-daunomycin conjugate under various conditions. FIG. 2 shows μg/ml release profile, over 48 hours, of daunomycin from the alginate-daunomycin conjugate under various conditions.

EXAMPLE 4

In vivo antitumor activity of alginate-cis-aconityl daunomycin

Male C57BL/6J mice were injected subcutaneously with $10^5$ viable B16f10 melanoma cells. Tumors were allowed to establish (approximate area 70 $mm^2$) and treated with a dosage of 5 mg each of free daunomycin, alginate-cis-aconityl-Dnm or a mixture of alginate and daunomycin per kg mouse, using a single intraperitoneal injection. Tumor growth and survival time was monitored.

Figure 3:
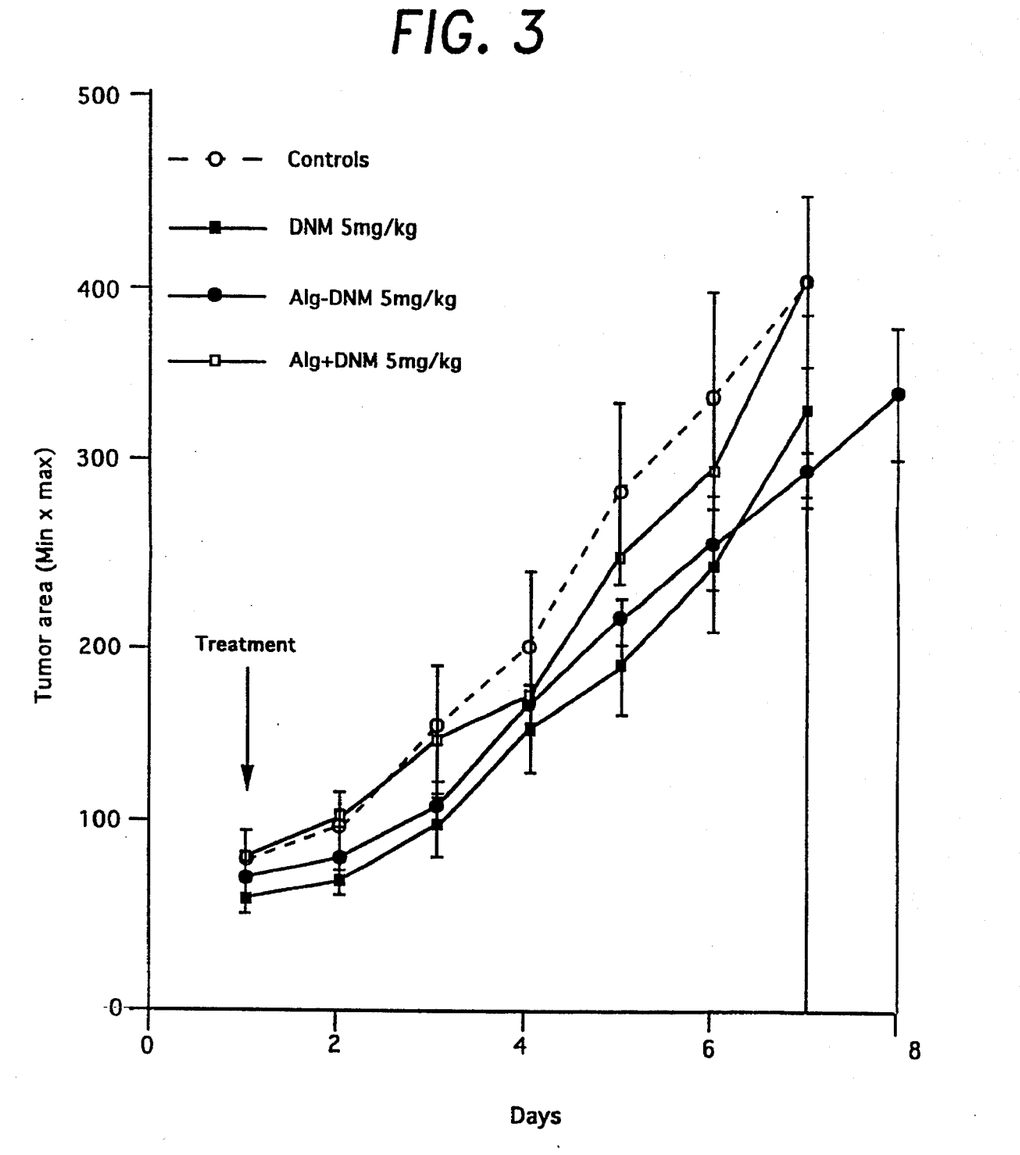
FIG. 3 shows the effect of daunomycin release on tumor cell growth.

Alginate-cis-aconityl-Dnm caused a significant decrease in the rate of minor growth. FIG. 3 shows tumor area growth over several days.

Alginate-cis-aconityl-Dnm caused an increase in life span (14.1%). Free daunomycin increased life span by 6.25% and a mixture of alginate and daunomycin increased life span by 4.25%. Some animals receiving free daunomycin showed signs of toxicity. None of the animals receiving alginate-cis-aconityl-Dnm showed signs of toxicity. It is possible, therefore, to administer larger conjugate doses than exemplified in the Example.

What is claimed is:

1. An alginate-therapeutically active agent conjugate which comprises:
   (a) an alginate, and
   (b) a therapeutically active agent, wherein the alginate and the therapeutically active agent are connected via a biodegradable spacer linkage.

2. A conjugate of claim 1 wherein the alginate has a molecular weight between about 2,000 and 1,000,000.

3. A conjugate of claim 2 wherein the alginate has a molecular weight between about 5,000 and 100,000.

4. A conjugate of claim 2 wherein the alginate has a molecular weight between about 200,000 and 1,000,000.

5. A conjugate of claim 3 wherein the alginate has a molecular weight between about 65,000 and 75,000.

6. A conjugate of claim 4 wherein the alginate has a molecular weight between about 600,000 and 800,000.

7. A conjugate of claim 1 wherein the alginate has attached functional amino groups.

8. A conjugate of claim 1 wherein the therapeutically active agent is a cytotoxic drug.

9. A conjugate of claim 8 wherein the cytotoxic drug is an anthracycline.

10. A conjugate of claim 9 wherein the anthracycline is daunombicin, doxorubicin, epirubicin or derivatives thereof.

11. A conjugate of claim 10 wherein the anthracycline is doxorubicin.

12. A conjugate of claim 1 wherein the therapeutically active agent is an antibiotic agent.

13. A conjugate of claim 12 wherein the antibiotic agent is amoxycillin or ampicillin.

14. A conjugate of claim 1 wherein the biodegradable spacer linkage is an acid labile linkage that is physiologically stable at vascular pH of about 7.4.

15. A conjugate of claim 14 wherein the acid labile linkage hydrolytically cleaves under acidic condition.

16. A conjugate of claim 15 wherein the acid labile linkage between the alginate and the therapeutically active agent is a cis-aconityl group having the formula.

17. A conjugate of claim 16 wherein the alginate has attached functional amino groups and the cis-aconityl group is attached to the alginate via peptide bond.

18. A method for manufacturing a medical preparation for the treatment of a neoplastic condition or a bacterial infection in mammals, said method comprising the step of combining a therapeutically-effective non-toxic amount of a compound as claimed in any one of claims 1 to 15, 17, or 16 with a pharmaceutical excipient.

19. A method for releasing a cytotoxic drug in an acidic environment comprising (a) introducing an alginate-cytotoxic drug conjugate comprising (i) an alginate, and (ii) a cytotoxic drug, wherein the alginate and the cytotoxic drug are connected via an acid labile linkage, to a pH environment of about 7.4;

(b) modifying the pH environment of the conjugate by decreasing the pH; and (c) hydrolyzing the alginate-cytotoxic drug conjugate linkage.

20. A method for releasing a cytotoxic drug in an acidic environment comprising (a) introducing an alginate-cytotoxic drug conjugate comprising (i) an alginate or alginate derivative, and (ii) a cytotoxic drug, wherein the alginate and the cytotoxic drug are connected via an acid labile linkage, into an acidic body compartment; and (b) hydrolyzing the alginate-cytotoxic drug conjugate linkage.

21. A method of claim 20 wherein the acidic body compartment is a stomach or a tumor cell.

22. A method for delivering a cytotoxic drug to a tumor which comprises (a) introducing to the tumor cell surface an alginate-cytotoxic drug conjugate comprising (i) an alginate, and (ii) a cytotoxic drug, wherein the alginate and the cytotoxic drug are connected via an acid labile linkage; and, (b) hydrolyzing the alginate-cytotoxic drug conjugate linkage in the low pH surroundings of the tumor surface to release the cytotoxic drug to the tumor surroundings and absorbing the cytotoxic drug through the cellular membrane.

23. A method for treating a neoplastic condition in a patient having a tumor which comprises (a) introducing an alginate-cytotoxic drug conjugate comprising (i) an alginate, and (ii) a cytotoxic drug, wherein the alginate and the cytotoxic drug are connected via an acid labile linkage, to a patient having a neoplastic condition; and (b) hydrolyzing the alginate-cytotoxic drug conjugate linkage in the low pH surroundings of the tumor surface to release the cytotoxic drug to the tumor surroundings and absorbing the cytotoxic drug through the cellular membrane.

24. A method for delivering a cytotoxic drug to a tumor which comprises (a) introducing an alginate-cytotoxic drug conjugate comprising (i) an alginate, and (ii) a cytotoxic drug, wherein the alginate and the cytotoxic drug are connected via an acid labile linkage, to the tumor cell surface;

(b) internalizing the conjugate by endocytosis into the tumor; and, (c) hydrolyzing the alginate-cytotoxic drug conjugate linkage in the low pH environment of the tumor interior to release the cytotoxic drug inside the tumor.

25. A method for treating a neoplastic condition in a patient having a tumor which comprises (a) introducing an alginate-cytotoxic drug conjugate comprising (i) an alginate, and (ii) a cytotoxic drug, wherein the alginate and the cytotoxic drug are connected via an acid labile linkage, to the tumor cell surface;

(b) internalizing the conjugate by endocytosis into the tumor; and, (c) hydrolyzing the alginate-cytotoxic drug conjugate linkage in the low pH enviromment of the tumor interior to release the cytotoxin inside the tumor.

26. A pharmaceutical composition comprising a therapeutically-effective non-toxic amount of at least one alginate-bioactive agent conjugate as claimed in any one of claims 1 to 15, 17 or 16 together with an inert, physiologically acceptable carrier.

27. A medical preparation containing a therapeutically-effective non-toxic amount of a compound as claimed in any one of claims 1 to 15, 17 or 16 and a pharmaceutical excipient.

28. A process for preparing an alginate-therapeutically active agent conjugate as claimed in any one of claims 1 to 15, 17, or 16 from an alginate within a selected molecular weight range, a linker compound for forming the biodegradable spacer linkage, and the therapeutically active agent, said method comprising the steps of:

(a) combining the linker with the therapeutically active agent to form a linker-modified therapeutically active agent;

(b) activating the alginate with 1-ethyl-3-(3-dimethylaminopropyl)-carbodiimide;

(c) combining activated alginate with ethylenediamine to form alginates having free primary amine groups (alginate-$NH_2$);

(d) activating the linker-modified therapeutically active agent with 1-ethyl-3-(3-dimethylaminopropyl)-carbodiimide; and (e) combining such activated linker-modified therapeutically active agent with said alginate-$NH_2$ to form the alginate-therapeutically active agent conjugate.

29. A process as claimed in claim 28 wherein the therapeutically active agent is a cytotoxic drug.

* * * * *